United States Patent [19]

Mehra-Palta

[11] 4,417,417

[45] Nov. 29, 1983

[54] CLONAL PROPAGATION OF GYMNOSPERMS

[75] Inventor: Asha Mehra-Palta, Monsey, N.Y.

[73] Assignee: International Paper Compay, New York, N.Y.

[21] Appl. No.: 307,635

[22] Filed: Oct. 1, 1981

[51] Int. Cl.³ .................................... A01G 1/00
[52] U.S. Cl. ............................................. 47/58
[58] Field of Search ................................... 47/58

[56] References Cited

U.S. PATENT DOCUMENTS

| | | | |
|---|---|---|---|
| 2,204,214 | 11/1940 | Hew Grace | 47/58 |
| 2,274,989 | 3/1942 | McKee | 47/58 |
| 4,038,778 | 8/1977 | Kadkade | 47/58 |
| 4,152,869 | 5/1979 | Jones | 47/58 |
| 4,217,730 | 8/1980 | Abo El-Nil | 47/58 |
| 4,346,794 | 10/1982 | Smeltzer et al. | 47/58 |
| 4,353,184 | 10/1982 | Abo El-Nil | 47/58 |

OTHER PUBLICATIONS

Bot. Gaz. 136, 196–200, (1975) Sommer, H. E., Brown, C. L. and Kormanik, P.
Bot. Gaz. 138, 298–304 (1977) Coleman, W. K. and Thorpe, T. A.
Can. J. Bot. 47, 687–699 (1969) Girouard, R. M.
Can. J. Bot. 53:1652–1657 (1975) Campbell, R. A. and Durzan, D. J.
Can. J. For. Res. 6, 240–243 (1976) Campbell, R. A. and Durzan, D. J.
CRC Report (1977) Cello, L. and Smeltzer, R. H.
N. Z. J. For. Sci. 7,199 (1977) Reilly, K. and Washer, J.
Physiol. Plant. 15:473–497 (1962) Murashige and Skoog.
Physiol. Plant. 22, 649–652 (1969) Basu, R. N. et al.
Plant and Cell Physiol. 17, 1347–1350 (1976) Cheng, T. Y.
Plant Science Letters, 5:97–102 (1975) Cheng, T. Y.
Planta 107:161 (1972) Gresshof, P. M. and Doy, C. H.
Proc. 15th Easter School in Agricultural Sciences, Univ. of Nottingham, Plenam Press (1968) Hess, C. E. In. W.7 Whittington (ed.).
Pulp & Paper, Jun. 1977, pp. 60–63.
Science, 198:306–307 (1977) Cheng and Vogu.
Tappi 60, 67 (1977) Mott, R. L., Smeltzer, R. H., Mehra-Palta, A., and Zobel, B. J.
Tappi 61, 37 (1978) Mehra–Palta, A., Smeltzer, R. H. and Mott, R. L.

*Primary Examiner*—Robert E. Bagwill
*Attorney, Agent, or Firm*—Robert M. Shaw

[57] ABSTRACT

A method of in vitro clonal propagation of plantlets from excised gymnosperm tissue in which the excised tissue is pulse treated on a nutrient medium containing at least about 10 mg/L, preferably at least about 20 mg/L, of a cytokinin for a time sufficient to induce formation of adventitious buds on the excised tissue and is then transferred to a nutrient medium free of exogenous growth factors and maintained thereon until the induced adventitious buds produce rootable shoots. The rootable shoots may then be rooted by conventional means but preferably are pulse treated on a nutrient medium containing a phenolic compound, preferably in an amount of at least about 5 mg/L, and an auxin, preferably in an amount of at least about 5 mg/L, for a time sufficient to induce formation of adventitious roots and then transferred to a nutrient medium free of exogenous growth factors until the shoots are rooted.

22 Claims, 23 Drawing Figures

FIG. 10
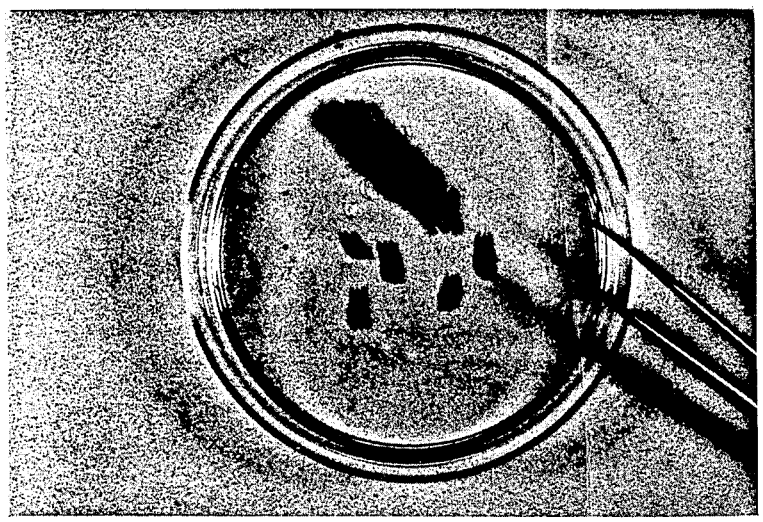
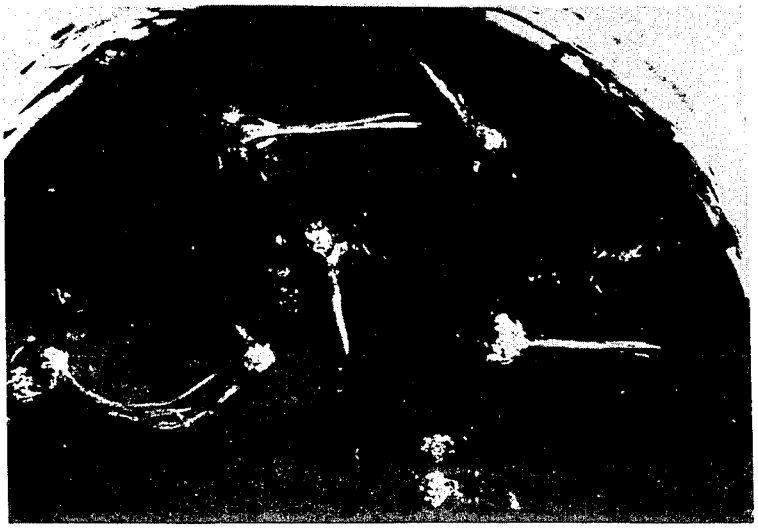
FIG. 11

FIG. 12
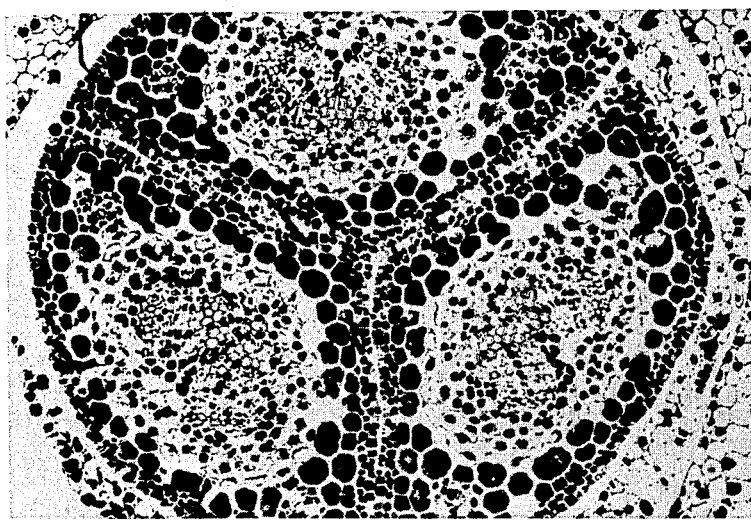
FIG. 13

FIG. 16
FIG. 17

FIG. 18
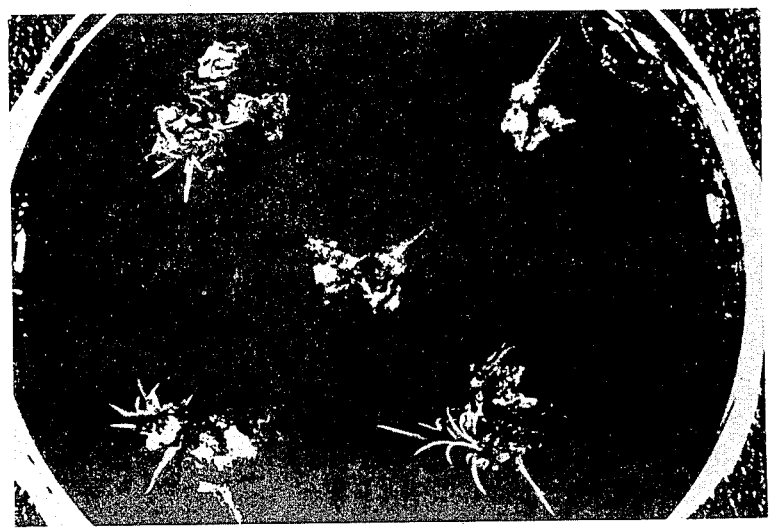
FIG. 19

CLONAL PROPAGATION OF GYMNOSPERMS

BACKGROUND OF THE INVENTION

This invention relates to the art of producing propagules from excised gymnosperm tissue. More particularly, this invention relates to an organogenetic method of in vitro clonal propagation of plantlets or propagules from excised gymnosperm tissue.

Approximately thirty species of gymnosperms, the so-called softwoods, comprise the great bulk of the commercially important timber species useful for construction lumber. Among these are the pines which include loblolly pine (*Pinus taeda*), slash pine (*Pinus elliotii*), longleaf pine (*Pinus palustris*), shortleaf pine (*Pinus echinata*), ponderosa pine (*Pinus ponderosa*), red pine (*Pinus resinosa*), jack pine (*Pinus banksiana*), Eastern white pine (*Pinus strobus*), Western white pine (*Pinus monticola*), sugar pine (*Pinus lambertiana*), lodgepole pine (*Pinus contorta*); Douglas-fir (*Pseudotsuga menziesii*); Western hemlock (*Tsuga canadensis*); Sitka spruce (*Picea glauca*); redwood (*Sequoia sempervirens*); the true firs including silver fir (*Abies amabilis*), grand fir (*Abies grandis*) noble fir (*Abies procera*), white fir (*Abies concolor*), balsam fir (*Abies balsamea*); and the cedars which include Western red cedar (*Thuja plicata*), incense cedar (*Libocedrus decurrens*), Port Orford cedar (*Chamaecyparis lawsoniona*), and Alaska yellow-cedar (*Chamaecyparis nootkatensis*), and Western larch (*Laryx occidentalis*).

Though not inclusive of all of the commercially important softwood species, the aforementioned group of conifers does include those pines which are generally considered to be commercially significant and which are or are becoming subject to intensive silvicultural management. Among these commercially significant pines, ponderosa pine, Western hemlock, Douglas-fir, and the four so-called southern yellow pines, slash, longleaf, shortleaf, and loblolly, are particularly important. Of this last group, loblolly pine and Douglas-fir have been the subject of intensive tree improvement breeding programs.

Loblolly pine, *Pinus taeda*, and Douglas-fir, *Pseudotsuga menziesii*, like many desirable species of trees, produce good seed crops only at infrequent and undependable intervals, and good cone crops typically occur only every five to seven years. In the normal course of events, a loblolly pine seedling produces male and female flowers when it is about 11 to 16 years old. When it does that, pollen from other trees will fertilize the female flowers, which will then produce seeds. About two years later, the seeds can be harvested and used to generate new plants. While the tree can pollinate some of its own female flowers so that some of the seedlings produced can be quite similar to the parent, none of the seedlings produced will be genetically identical.

Initially, the production of seedlings depended on wild seed which is drawn from an enormously varied gene pool. It was not long before foresters began to recognize that some seedlings grew far better in localized environments than others. For example, in the Douglas-fir region, it was found to be important to plant seedlings at the same approximate altitude from which the seed had been obtained. Soon it was realized that many other tree characteristics were heritable and while these traits vary from species to species, among them might be mentioned growth rates, the tendency to have straight or crooked stems, wood density, and light as opposed to heavy limbs. Nursery managers thus began searching their forests for and collecting seeds from wild trees that possessed one or more desirable characteristics. However, depending on the species, it may take from 15 to 50 years for a new generation to produce seeds of its own and several generations of breeding are required in order to maximize genetic improvement.

Accordingly, less time consuming methods have been sought to obtain genetically superior trees. To this end, vegetative propagation of pines, such as loblolly pine, by grafting or rooting of stem cuttings and needle fascicles has been carried out but these methods are inefficient and are not without their difficulties. Grafting is labor intensive and the percentage of success tends to be low because of graft or stock-scion incompatibility problems and, with rooting, the frequency of rooting tends to be very low and very young trees must generally be employed.

Accordingly, a goal of current research efforts is the development of reliable asexual methods for mass-producing identical copies of superior trees in great numbers. The advantages to be derived from such methods, in addition to the apparent economic advatages, include the potential for a drastic reduction in the time required to produce a second generation of trees from superior seedlings from a minimum of about 15 years to less than about 2 years.

Since a single cell in any plant or animal contains all of the genetic information necessary to replicate the entire organism, research efforts have tended in recent years to focus on the production of genetically superior seedlings by producing many plantlets from a single cluster of cells excised from a genetically superior tree, which method is commonly referred to in the art as clonal propagation or tissue-culture replication. The first tree reported to be produced by tissue-culture techniques was a quaking aspen at the Institute of Paper Chemistry in 1968. It has been discovered, however, that tissue-culture replication of conifers is not as easily accomplished.

Successful asexual clonal propagation techniques to date have been based on the biological processes known as organogenesis and embryogenesis. Organogenesis includes the initiation of shoots from meristematic centers induced in cultured tissue explants and the subsequent rooting of these shoots. As the method is generally employed, a portion of a donor plant is excised, sterilized and placed on a growth medium. The tissue most commonly used is a portion of young cotyledon from newly sprouted seeds or the intact embryo dissected from a seed. A much lower degree of success has been reported when tree leaves or stem tissues are cultured.

The growth medium consists of a basal nutrient medium of mineral salts and organic nutrients to which plant hormones have been added. One commonly used basal medium is that of Murashige and Skoog [Physiol. Plant. 15:473–497 (1962)]. This may be modified by addition of sucrose, myo-inositol, and thiamine [Cheng, T. Y., *Plant Science Letters*, 5:97–102 (1975)]. Various cytokinins and auxins are generally added to the basal medium to induce cell differentiation and growth. After an initial callus growth has formed which contains bud primordia, the plant material can be placed on a succession of different mediums that promote bud growth and shoot elongation. The shoot elongation medium may be free of hormones to reduce competing callus growth. The elongated shoots are excised and placed on a rooting medium consisting of the basal medium and generally with an auxin as the only exogenous hormone. When root primordia have formed, the shoots may be nourished on a medium free of added hormones in order to encourage root growth. The resultant plantlets are removed from the artificial media into a natural or synthetic soil mixture.

In the embryogenesis process, a group of cells become organized into a bipolar embryoid which will, in a favorable environment, develop bud primordia at one end and root primordia at the opposite end. One commonly reported route to production of plantlets by embryogenesis has been through suspension culture wherein groups of cells are suspended in a gently agitated liquid medium containing various plant growth hormones until bipolar embryoids are differentiated and developed. The embryoids are then placed on a nutrient medium for further development into plantlets.

DEFINITIONS

As used herein, the following terms have the indicated meanings:

Adventitious

Organs that develop in abnormal and unpredictable locations where organ primordia do not normally exist.

Auxins

Plant hormones that promote cell division and growth. Among the known auxins are the following: α-napthaleneacetic acid (NAA), indole-3-acetic acid (IAA), indole-3-butyric acid (IBA), indole-3-propionic acid (IPA) and 2,4-dichlorophenoxyacetic acid (2,4-D).

Callus

A growth of unorganized and either unconnected or loosely connected plant cells generally produced by culturing an explant.

Clonal Propagation

Used interchangeably with "Tissue Culture" as defined herein.

Cytokinins

Plant hormones that effect the organization of dividing cells and function in the transmission of information from DNA for protein formation. Among the known cytokinins are the following: 6-benzylaminopurine (BAP), Zeatin (Z), Kinetin (K), and 6-(3-methyl-2-butenylamino/purine (2iP).

Embryogenesis

The development of embryoids from tissue that would not ordinarily organize into defined meristemic centers. Embryoids are believed to develop from single plant cells as a result of a particular hormonal/nutritional regimen.

Embryoid

An asexually reproduced bipolar group of organized cells having defined meristemic centers that can ultimately develop into plantlets. It differs from seed embryo primarily in the asexual method of development which gives genetic identity to the tissue donor.

Excised Tissue or Explant

A piece of tissue taken from a donor plant (also referred to herein as the "tissue donor") for tissue culture.

Gresshof and Doy Medium (GD or GD medium)

A basic nutrient medium [Gresshof, P. M., and Doy, C. H., Planta 107:161 (1972)] which, as modified and used herein in the examples, contained the following components in the indicated concentrations: $KNO_3$ (1000 mg/L), $MgSO_4.7H_2O$ (250 mg/L), $(NH_4)_2SO_4$ (200 mg/L), $CaCl_2.2H_2O$ (150 mg/L), KCl (300 mg/L), $NaH_2PO_4.H_2O$ (90 mg/L), $Na_2HPO_4$ (30 mg/L), $MnSO_4.H_2O$ (10 mg/L) $ZnSO_4.7H_2O$ (3 mg/L), $H_3BO_3$ (3 mg/L), KI (0.75 mg/L), $CuSO_4.5H_2O$ (0.25 mg/L), $Na_2MoO_4.2H_2O$ (0.25 mg/L), $CoCl_2.6H_2O$ (0.25 mg/L), $FeSO_4.7H_2O$ (27.8 mg/L), $Na_2EDTA$ (37.3 mg/L), myo-inositol (10 mg/L), thiamine HCl (1 mg/L), nicotinic acid (0.1 mg/L), pyridoxin HCl (0.1 mg/L), sucrose (20,000 mg/L), and agar (9,000 mg/L).

This nutrient medium is exemplary of those known in the art and hence any such medium similarly employed in the art may be substituted for the GD medium. As is known to those skilled in the art, the concentrations of components may vary and components may be deleted from or added to those listed above. The GD medium is employed at various concentrations in combination with various plant growth regulators. As used herein, "GD" or "GD medium" preceded by a fraction indicates that the concentrations of the components in the medium are that fraction of the above-indicated concentrations.

Meristem

A group of tissue-forming cells capable of further directed development into plant organs such as buds, shoots and roots.

Morphogenesis

The origin and development of organs or parts of organisms. The term encompasses both organogenesis and embryogenesis.

Needle Fascicles

The clusters of individual green leaves, or needles, on a pine tree. Each fascicle has two to five needles and a brown wrapping at the base.

Organogenesis

The formation and development of organs such as buds, shoots and roots from meristemic centers in tissues that would not ordinarily organize into the particular organ. One way in which this process differs from embryogenesis is that a bipolar group of organized cells having defined meristemic centers which can develop directly into a plantlet is not produced but rather individual organs are produced by sequential induction of meristemic centers. Thus, adventitious buds are induced in callus tissue, elongate into shoots, and then roots are induced in the adventitious shoots and allowed to grow out resulting in a plantlet.

Phenolics or Phenolic Compounds

Plant growth regulators. Among the known phenolics are the following: Ferulic acid (FA), Coumaric acid (CA), p-hydroxybenzoic acid (PBA), Catechol (CTO), Chlorogenic acid (CLA), Isochlorogenic acid (ICA), Vanillic acid (VA), and Caffeic acid (CFA).

Plantlet or Propagule

A rooted shoot asexually reproduced by tissue culture and capable of being transplanted into artificial or natural soil medium for continued growth.

Tissue Culture

The process according to which tissue excised from a donor plant is nourished on a series of culture media to produce plantlets genetically identical to the donor. Also referred to herein as "Clonal Propagation".

REPORTED DEVELOPMENTS

Production of plantlets from explants of the following tree species employing tissue culture techniques have been reported in the scientific literature. *Pinus palustris* [Sommer, H. E., Brown, C. L. and Kormanik, P. 1975 Bot. Gaz. 136, 196]; *Pseudotsuga menziesii* [Cheng, T. Y. 1975. Plant Sci. Letters 5, 97]; *Picea glauca* [Campbell, R. A. and Durzan, D. J. 1976. Can. J. For. Res. 6, 240]; *Pinus radiata* [Reilly, K. and Washer, J. 1977. N.Z.J. For. Sci. 7, 199]; *Thuja plicata* [Coleman, W. K. and Thorpe, T. A. 1977. Bot. Gaz. 138, 298]; *Tsuga heterophylla* [Cheng, T. Y. 1976. Plant & Cell Physiol. 17, 1347]; and *Pinus taeda* [Mehra-Palta, A., Smeltzer, R. H. and Mott, R. L. 1978. Tappi 61, 37].

The aforementioned reports primarily discuss the regeneration of plantlets and do not disclose the clone size that can be obtained from select genotypes. Bud induction was generally effected by prolonged culture on cytokinin medium and only a small percentage of the buds grew out into elongated shoots and formed roots.

U.S. Pat. No. 4,217,730 discloses a method of producing embryoids from plants of the Subdivision Gymnospermae through the use of tissue culture in a liquid suspension and, as such, is directed to an embryogenetic process which, as previously discussed, is distinctly different from the organogenetic methods of which the present method forms a part. However, the patent does disclose a comparative example which is said to employ the general organogenetic technique of Cheng and Vogu [*Science,* 198:306–307 (1977)].

Approximately 25 sterilized cotyledon explants were placed on the surface of a light-weight, porous felt in contact with a liquid bud induction medium consisting of a basic nutrient medium and 1.0 mg/L each of BAP, IAA and IBA, in a sealed container for 45 days at 21° C. in a 16-hour light and 8-hour dark schedule to produce a number of meristemoids for ultimate development into bud meristems. The liquid bud induction medium was then aspirated to the extent possible (80 to 90%) and replaced with a shoot production medium lacking any plant hormones for about 90 days at 21° C. in a 16-hour light and 8-hour dark schedule until the meristemoids developed into short shoots about 5 to 10 millimiters long.

The shoots were then excised and transferred individually into a sterile medium, also lacking any plant hormones, on agar plates. The shoots, about 25 adventitious shoots per 8 cm diameter agar plate, were grown under conditions similar to the above for about two months until the shoots were about 20-25 mm high. No roots had developed at that point. The shoots were then either transferred to unsterile soil for rooting or to a fourth medium consisting of a basic nutrient medium, 3.0 mg/L of IBA, and 0.01 mg/L of NAA for 30 to 45 days under growth conditions similar to those described before and then transplanted, still normally without visible roots, into soil and maintained for several weeks at or near 100% relative humidity until full rooting occurred.

U.S. Pat. No. 4,152,869 discloses a process for propagating woody plant material of apple, plum or cherry in vitro in which shoot tips are cultured on a nutrient medium including 0.5 or 1.0 mg/L of a cytokinin (BAP), 0.1 mg/L of an auxin (IBA) and 162 mg/L of a phenolic compound (phloroglucinol) for about 4 weeks, and then transferred to the same but fresh medium for a further 5 weeks at which time between 20 and 25 shoots have developed from each initial shoot tip. The shoots were excised and rooted for 6 weeks on the same or a similar nutrient medium from which the cytokinin was omitted, and the rooted shoots then placed in pots of compost. The number of adventitious buds produced per shoot tip, the percentage of adventitious buds forming shoots, the percentage of shoots forming roots and the application of the process to tissue from trees other than apple, plum or cherry are not discussed.

Previously reported techniques or methods for inducing adventitious buds include culturing intact embryos for 5 to 6 weeks on a medium comprising GD, BAP (10 mg/L) and NAA (0.01 mg/L) [Mott, R. L., Smeltzer, R. H., Asha Mehra-Palta, and Zobel B. J.; 1977; Tappi Vol. 60, pp. 62–64]; culturing intact embryos on a medium comprising GD, BAP (10–20-mg/L) and ABA (0.03–0.3 mg/L) [Cello, L. and Smeltzer, R. H.; 1977; CRC report]; and culturing excised cotyledons for 6 to 7 weeks on GD, 0.1 to 5 mg/L of a cytokinin, such as BAP, and 0 to 0.5 mg/L of an auxin, NAA [Mehra-Palta, A., Smeltzer, R. A. and Mott, R. L.; 1978; Tappi, Vol. 61, pp. 37–40]. These previously reported techniques possess certain disadvantages. A limited number of adventitious buds were induced (an average of 6 buds/embryo for intact embryos and 15 buds/embryo for excised cotyledons) and only up to about 50% of the adventitious buds from intact embryos and up to about 20% of the adventitious buds from excised cotyledons elongated to form rootable shoots more than 5 mm long. The remaining shoots did not survive.

The use of phenolics in combination with auxins to obtain increased rooting over that obtained with auxins alone has been reported for in situ rooting of cuttings from plant species like *Erantheum* [Basu, R. N. et al. 1969. Physiol. Plant. 22, 649–652] and *Hedera helix* [Hess, C. E. 1968 In. W. J. Whittington (ed.), Proc. 15th Easter School in Agricultural Sciences, Univ. of Nottingham, Plenum Press] but, in these species, roots form easily and, in fact, preformed root primordia are present in the stem. The Hess article reports that the juvenile tissue of *Hedera helix* contains isochlorogenic acid (a phenolic compound) and it has also been reported that the juvenile tissue contains chlorogenic acid (another phenolic compound) [Girouard, R. M. 1969. Can. J. Bot. 47, 687–699]. The articles do not disclose in vitro rooting, the rooting of adventitious shoots nor the use of a combination of auxin and phenolic compounds in the in vitro rooting of adventitious shoots.

OBJECTS OF THE INVENTION

It is an object of the present invention to provide a method of in vitro clonal propagation of excised gymnosperm tissue.

It is another object of the present invention to provide a method of inducing a high percentage of adventitious buds on excised gynosperm tissue.

It is yet another object of the present invention to provide a method of inducing high frequency root formation on adventitious shoots.

It is a further object of the present invention to provide such a methodology which allows for mass propagation of genetically superior pine trees and in less time than has heretofore been practicable with prior methods.

SUMMARY OF THE INVENTION

The present invention is directed to a method of in vitro clonal propagation of plantlets from excised gymnosperm tissue. Excised gymnosperm tissue is pulse treated on a nutrient medium containing at least about 10 mg/L, preferably at least about 20 mg/L, of a cytokinin for a time sufficient to induce formation of adventitious buds on the excised tissue. The pulse treated tissue is then transferred to a nutrient medium free of exogenous growth factors. The pulse treated tissue is maintained on this nutrient medium until the induced adventitious buds produce rootable shoots.

The rootable shoots may then be rooted by conventional means but, according to a preferred method which forms a part of the present invention, the rootable shoots are then rooted by pulse treatment on a nutrient medium containing a phenolic compound, preferably in an amount of at least about 5 mg/l, more preferably in an amount of from about 5 mg/l to about 10 mg/l, and an auxin, preferably in an amount of at least about 5 mg/l, more preferably in an amount of from about 5 mg/l to about 10 mg/l for a time sufficient to induce formation of adventitious roots on the shoots. The treated shoots are then transferred to a nutrient medium free of exogenous growth factors and are preferably maintained on this medium until the roots grow out or elongate. The rooted shoots, which at this point are known as plantlets or propagules, may be transferred or transplanted into soil for continued growth.

BRIEF DESCRIPTION OF THE DRAWINGS

FIG. 10 is a photograph of a shoot of a pine tree with needle fascicles at developmental stage (3) and also shows a number of needle fascicles which have been excised for treatment.

FIG. 11 is a photograph of excised needle fascicles three weeks after treatment on bud growth medium and shows the bases of the needle fascicles swollen due to activation of bud primordia.

FIG. 12 is a photograph of one of the needle fascicles of FIG. 11 on a magnified scale and shows multiple bud primordia.

FIG. 13 is a photograph of a magnified view of a transverse section of the basal region of a control needle fascicle.

FIG. 16 is a photograph of a magnified view of one of the shoot primordia of FIG. 15.

FIG. 17 is a photograph of a primary needle (i.e., scale leaf) 1 to 2 millimeters long which has been excised from a newly formed shoot and cultured, as a comparative example, on bud induction medium for six weeks. This photograph shows that under this treatment buds were mostly formed near the cut ends of the primary needles.

FIG. 18 is a photograph showing adventitious bud primordia developed on bud growth medium (½ GD and charcoal 1%) after pulse-treatment and removal of the needle fascicle sheath.

FIG. 19 is a photograph showing a number of adventitious shoots on bud growth medium after ten weeks of culture in which each group represents shoots formed from 1 needle fascicle.

DESCRIPTION OF PREFERRED EMBODIMENTS

Figure 1:
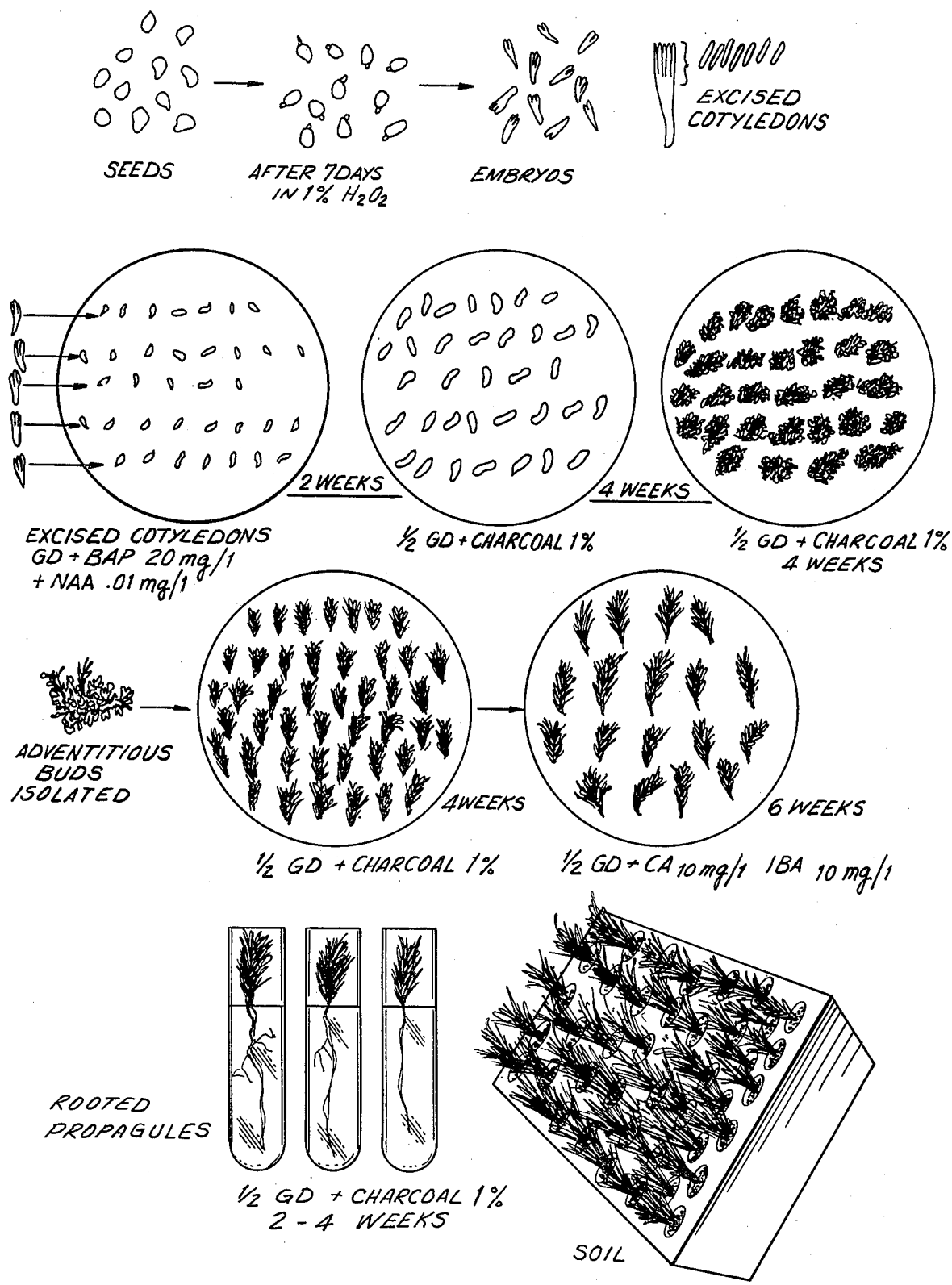
FIG. 1 is a schematic diagram of a process inclusive of a preferred embodiment of the present invention and showing the use of cotyledons, a preferred excised gymnosperm tissue, and preferred concentrations, nutrient media and treatment times.

The present method may be employed to produce a plantlet, from excised tissue, that is genetically identical to the tissue donor. While the tissue donor may be any gymnosperm, it is preferred that the tissue donor be a conifer and, in particular, one of the aforementioned softwoods. More preferably, the tissue donor is selected from those trees belonging to the family Pinaceae and, in particular, from the group consisting of loblolly pine (*Pinus taeda*) and Douglas-fir (*Pseudotsuga mensiesii*). Loblolly pine is a particularly preferred tissue donor.

The excised tissue or explant is preferably selected from the group consisting of cotyledons, needle fascicles, intact seed embryos, needles, shoot tips, apical buds, and hypocotyls. More preferably, the explant will be selected from the group consisting of cotyledons and needle fascicles, and it is particularly preferred to employ cotyledons.

Prior to treatment, the excised gymnosperm tissue is preferably washed and surface sterilized. One preferred means of preparing the tissue is to wash it with a 1% solution of a commercial detergent, such as Alconox, for about two minutes followed by rinsing with tap water for about two hours followed by surface sterilization by treatment with a 10% solution of a commercial bleach, such as Clorox, for about 10 to about 15 minutes. Preferably, the tissue is then rinsed one or more times with sterile distilled water.

The explant is cultured or treated by being placed on a basic nutrient medium containing a cytokinin ("bud induction medium") for a time sufficient to induce formation of adventitious buds on the excised tissue. The medium may preferably contain a low concentration of an auxin. This treatment is referred to herein as "pulse treatment" or "pulse treating", since the time that the explant is in contact with the bud induction medium is only that time which is required to induce formation of adventitious buds on the excised tissue and, hence, is a short period of time relative to the treatment times heretofore generally employed for bud induction with plant growth factor-containing media.

Typically, the treatment time is less than about 5 weeks and preferably is from about 1 week to about 4 weeks. A particularly preferred treatment time is from about 2 weeks to about 3 weeks. The pulse treatment time will generally vary within the range of from about 1 week to about 4 weeks depending on the nature of the excised tissue and the species of the tissue donor. After pulse treatment on the bud induction medium, the pulse treated explant is immediately transferred to a basic nutrient medium containing no exogenous growth factors ("bud growth medium"). The pulse treated explant is maintained or cultured on this bud growth medium for a time sufficient to grow or produce rootable shoots from the induced adventitious buds.

Environmental factors such as temperature and light are not particularly critical but the optimal environmental conditions for the culture of excised gymnosperm tissue and induced buds, which are known to persons skilled in the art, should be employed with the method of the present invention during bud induction and bud growth.

The cytokinin may be any cytokinin known or discovered to function as a growth factor for gymnosperm tissue. Preferably, the cytokinin will be selected from the group consisting of 6-benzylaminopurine, zeatin, Kinetin, and 2iP, and mixtures thereof. A particularly preferred cytokinin is 6-benzylaminopurine. The cytokinin is present in an amount of at least about 10 mg/L, preferably at least about 20 mg/L. More preferably, the cytokinin is present in an amount of from about 20 mg/L to about 200 mg/L, and even more preferably in an amount of from about 20 mg/L to about 100 mg/L.

The cytokinin concentration will tend to vary with variations in the cytokinin employed as well as with variations in the species of the tissue donor and the nature of the explant. For example, with cotyledons, lesser amounts, that is, amounts of about 20 mg/L, are preferred whereas with more nature tissues, such as needle fascicles, cytokinin concentrations of from about 50 mg/L to about 100 mg/L are preferred, though amounts between about 25 mg/L and 100 mg/L may be employed.

When an auxin is included in the bud induction medium, any auxin known or discovered to function as a growth factor for gymnosperm tissue may be employed. Preferably, the auxin is selected from the group consisting of indole-3-butyric acid, indole-3-acetic acid, 2,4-dichlorophenoxyacetic acid, and α-naphaleneacetic acid, and mixtures thereof. Two particularly preferred auxins are α-napthaleneacetic acid and indole-3-butyric acid. The auxin concentration is preferably within the range of from about 0.01 mg/L to about 0.1 mg/L. More preferably, the auxin concentration will be from about 0.01 mg/L to about 0.05 mg/L. A particularly preferred concentration is about 0.01 mg/L.

As the basic nutrient medium, any medium free of exogenous plant growth factors and containing nutrients required by gymnosperm tissue may be employed. One particularly preferred basic nutrient medium is the aforementioned GD medium, but others, such as the medium of Murashige and Skoog [Physiol. Plant. 15: 473–497 (1962)] may be employed. The various components and concentrations thereof in such basic nutrient media are generally known in the art, as are modifications of these media to enhance the growth of particular species and organs. The basic nutrient medium is free of exogenous plant growth factors although the tissue cultured on the nutrient medium may contain endogenous plant growth factors, such as cytokinins, auxins and phenolics. A preferred bud induction medium comprises GD medium and a cytokinin in the indicated range of concentrations and more preferably, it also includes an auxin. A preferred bud growth medium comprises ½ GD and charcoal (1%) and is free of exogenous growth factors.

The pulse treated explants are maintained on the bud growth medium until the induced adventitious buds produce rootable shoots. This time will vary depending on the species, the type of explant, and environmental factors, such as light and temperature. Generally, the pulse treated explants will be maintained on the bud growth medium until the adventitious buds have produced shoots at least about 5 mm in length, at which time they may be considered rootable, and, more preferably, at least about 10 mm in length and having a stem 1–2 mm in length. The shoots should be morphologically well defined before being transferred for rooting. Since shoots may be produced and may grow at different rates, as certain shoots achieve a desired length they may be separated or isolated from the explant and transferred to a root induction medium, while the remaining shoots and buds are left on the explant for continued growth, either on the same or on fresh bud growth medium. A preferred method is to culture the adventitious buds for 3 cycles of 4 weeks each on the bud growth medium.

When employing needle fascicles as the explant, frequency of bud induction may tend to vary depending on the developmental stage of the needle fascicles. As needle fascicles develop, they may be thought of as passing through five different developmental stages which, for convenience, may be summarized as follows:

(1) the needle fascicles are in the form of small primordia which are tightly enclosed within the sheath;

(2) the needle fascicle primordia are slightly elongated but still enclosed by the sheath;

(3) the needle fascicle primordia are within the sheath but ready to emerge;

(4) the needle fascicles have emerged from the sheath and are about one to about two centimeters in length; and (5) the needle fascicles are fully elongated. It is preferred, in order to obtain optimal results, to treat needle fascicles which are in developmental stage (3) and when employing needle fascicles from developmental stage (3), optimal bud induction has been observed when the needle fascicles are pulse treated on BAP (25 mg/L) and NAA (0.01 mg/L) for three weeks. The sheaths are then removed before the needle fascicles are transferred to the bud growth medium.

When the shoots are sufficiently well developed for rooting they are removed from the bud growth medium and may be rooted by conventional means, such as placing the shoots directly into sterile soil or transferring the shoots to root induction medium comprising a basic nutrient medium and one or more auxins, such as 3 mg/L of IBA and 0.01 mg/L of NAA, or 0.1 mg/L of BAP and 0.1 mg/L of NAA, for generally about 8 weeks, then transferring the treated shoots either to soil or to a nutrient medium free of exogenous plant growth factors. The percentage of shoots rooted ("root induction frequency") when treated on such root induction medium may be as high as 50%, but ranges of 20% to 40% are more common, and averages of 35% have been reported.

It has been discovered, however, that by pulse treating rootable shoots on a nutrient medium containing a phenolic compound and an auxin ("root induction medium") for a time sufficient to induce formation of adventitious roots on the shoots and then immediately transferring the treated shoots from this root induction medium to a nutrient medium free of exogenous growth factors ("root growth medium"), root induction frequencies of about 50% to about 90%, may be obtained, even though the rootable shoots are treated with or cultured on the plant growth factor-containing medium for a shorter period of time than has heretofore been generally employed in the art for root induction. Preferably, the rootable shoots are pulse treated for from about 2 weeks to about 6 weeks and, more preferably, from about 4 weeks to about 6 weeks. The treated shoots are maintained or cultured on a nutrient medium free of exogenous growth factors until the roots elongate. The rooted shoots, or propagules, are then transferred into soil, preferably under an initial mist-like environment for about 2-4 weeks or until new shoot growth is initiated, and then maintained under standard greenhouse conditions, typically for from about 6 to about 8 months, until ready for outplanting (i.e., transplanting in the field).

As in the case with bud induction and bud growth, environmental factors such as light and temperature are not particularly critical but the optimal conditions for the culture of rootable shoots and rooted shoots, which are known to persons skilled in the art, should be employed with the method of the present invention during root induction and root growth.

The basic nutrient medium employed in the root induction medium and the root growth medium may be any of the nutrient media discussed for inclusion in the bud induction medium and the bud growth medium of the present invention. The preferred root growth or elongation medium, like the preferred bud growth medium, contains ½ GD and charcoal (1%) and is free of exogenous plant growth factors. The preferred root induction medium contains ½ GD, a phenolic and an auxin.

The use of root induction media containing a combination of a phenolic compound with an auxin results in greater root induction frequency and the ability to use shorter treatment times than may be used for root induction with media containing, as the plant growth factor, either one or more auxins or one or more phenolic compounds. The use of a phenolic compound as the only exogenous factor may tend to be inhibitory to rooting. As the phenolic compound, any of the phenolic compounds which have been reported to be endogenously present in gymnosperms may be employed. Preferably, the phenolic compound is selected from the group consisting of coumaric acid, ferulic acid, p-hydroxybenzoic acid, catechol, vanillic acid, and caffeic acid, and mixtures thereof. Particularly preferred phenolic compounds are coumaric acid and ferulic acid. The phenolic compound is preferably present in an amount of at least about 5 mg/L, more preferably from about 5 mg/L to about 50 mg/L, and even more preferably from about 5 mg/L to about 10 mg/L. Concentrations in excess of 50 mg/L may be employed but, as this concentration is exceeded, growth of the shoots may tend to be inhibited. A particularly preferred amount is about 10 mg/L.

The auxin may be any of the auxins, or any combination thereof, discussed for inclusion in the bud induction medium of the present invention. The auxins preferred for use in the bud induction medium are also preferred for use in the root induction medium. The auxin is preferably present in an amount of at least about 1 mg/L, more preferably, from about 5 mg/L to about 50 mg/L, and, even more preferably from about 5 mg/L to about 10 mg/L. Concentrations in excess of 50 mg/L may be employed, but callusing is greatly increased. A particularly preferred combination of phenolic and auxin is about 10 mg/L of coumaric acid and about 10 mg/L of indole-3-butyric acid. The concentrations of phenolic compound and auxin may tend to vary with variations in the species of the tissue donor and with the type of explant.

The present method allows for the asexual production of 30 to 40 plantlets from a single explant which demonstrate phenotypic uniformity and fidelity to parental genotype. Average clones of twenty plantlets can be routinely produced, and plantlets have been transferred to soil and carried through 5 months of greenhouse culture with less than twenty percent mortality. With the present method, greater root induction frequency, and hence, lesser clonal effects are observed than have been observed for previous techniques. Additionally, the present method is less susceptible to seasonal influence of environmental factors than has been observed for in situ techniques.

The following examples present illustrative but nonlimiting embodiments of the present invention. Comparative examples are also presented.

EXAMPLES

In the following examples, unless otherwise noted, the nutrient medium employed was the GD medium. The environmental conditions of light and temperature generally employed in the examples were: about 25±2° C. and constant light supplied by GROLUX lamps at an intensity of about 300 foot candles, although some variations of light and temperature were employed which are well within the skill of those persons skilled in the art. In some instances a higher percentage of rooting was obtained when the environmental conditions were: 16 hours of light at 25° C. followed by 8 hours of darkness at 10° C. supplemented with incandescent light.

EXAMPLE 1

To determine the influence of genetic differences and of the cytokinin concentration on bud induction potential, excised needle fascicles from three seed families, (7-105), (7-56) and (7-88), were treated according to the method of the present invention at a constant auxin concentration but at three different cytokinin concentrations and the percentage of needle fascicles making buds after pulse treatment for three weeks with each cytokinin/auxin combination recorded. As a control, excised needle fascicles from each seed family were treated, according to a method exemplary of methods previously employed in the art, for six weeks on a nutrient medium containing BAP (2.5 mg/l) and NAA (0.01 mg/l). The results are summarized in Table 1 below.

TABLE 1

| Family | Time of Treatment (weeks) | % needle fascicles making buds on 0.01 mg/l NAA plus BAP at a concentration of | | | |
|---|---|---|---|---|---|
| | | 25 mg/l | 50 mg/l | 100 mg/l | 2.5 mg/l (control) |
| (7-105) | 3 | 67 | 42 | 16 | — |
| Control | 6 | — | — | — | 13 |
| (7-56) | 3 | 66 | 50 | 39 | — |
| Control | 6 | — | — | — | 10 |
| (7-88) | 3 | 42 | 41 | 21 | — |
| Control | 6 | — | — | — | 15 |

The needle fascicles treated with 25 mg/l BAP and 0.01 mg/l NAA were transferred to a nutrient medium containing no exogenous growth factors and the frequency of growth by adventitious buds induced by the pulse treatment method recorded. The frequency of bud growth for buds induced by the control technique of 6 weeks treatment on BAP at 2.5 mg/l and NAA at 0.01 mg/l was also recorded. The results are summarized in Table 2, below.

TABLE 2

| Treatment | Frequency of Bud Growth |
|---|---|
| Pulse treatment on 25 mg/l BAP + 0.01 mg/l NAA for 3 weeks; transfer to growth medium | 70–80% |
| Treatment on 2.5 mg/l BAP + 0.01 mg/l NAA for 6 weeks | 10–20% |

EXAMPLE 2

Sets of excised needle fascicle shoots from undefined seed families were pulse treated for three weeks, one set on a nutrient medium containing BAP (50 mg/l) and NAA (0.01 mg/l), and the other set on a nutrient medium containing BAP (100 mg/l) and NAA (0.01 mg/l), to induce formation of adventitious buds, and the induced adventitious buds were then grown on a nutrient medium containing no exogenous growth factors. The frequency of root induction on the resultant shoots was then determined by treating shoots for from 4 to 6 weeks on one of two nutrient media each containing the phenolic CA and the auxin IBA but differing in the concentration of the phenolic. The treated shoots were then transferred to nutrient media free of exogenous growth factors and the percentage of shoots that rooted was determined. The results are summarized in Table 3, below.

TABLE 3

| Bud Induction Medium | Root Induction Medium | % of Shoots Rooted |
|---|---|---|
| 50 mg/l BAP + 0.01 mg/l NAA | Coumaric Acid (10 mg/l) + indole-3-butyric acid (10 mg/l) | 67 |
| 100 mg/l BAP + 0.01 mg/l NAA | Coumaric Acid (10 mg/l) + indole-3-butyric acid (10 mg/l) | 53 |
| 50 mg/l BAP + 0.01 mg/l NAA | Coumaric Acid (5 mg/l) + indole-3-butyric acid (5 mg/l) | 35 |
| 100 mg/l BAP + 0.01 mg/l NAA | Coumaric Acid (5 mg/l) + indole-3-butyric acid (5 mg/l) | 60 |

EXAMPLE 3

Excised needle fascicles were pulse treated for three weeks on a nutrient medium containing BAP (50 mg/l) plus NAA (0.01 mg/l). Control groups of needle fascicles were treated for 6 to 8 weeks on a nutrient medium containing BAP (2.5 mg/l) and NAA (0.01 mg/l). The frequency of bud induction for the pulse treated needle fascicles was observed to be 40 to 50% as compared to 10 to 20% for the control treatment. Additionally, about 25% of the pulse treated needle fascicle making buds were observed to have 3 buds per needle fascicle and some of these formed 10 buds per fascicle, whereas, with the control treatment, an average of 1 bud and a maximum of 3 buds per needle fascicle were observed.

EXAMPLE 4

Intact embryos and excised cotyledons were pulse treated on a nutrient medium containing BAP (20 mg/l) and NAA (0.01 mg/l) for 1 hour, 24 hours, 1 week and 2 weeks, and then transferred to a bud growth medium ($\frac{1}{2}$GD+charcoal 1%). No buds were obtained on the intact embryos pulse treated for 1 hour and 24 hours. A few buds were formed on embryos treated for 1 and 2 weeks. The excised cotyledons pulse treated for 1 and 2 weeks initiated a higher percentage of adventitious buds as compared to the controls that were cultured for 8 weeks on standard bud induction medium; GD, BAP (1 mg/l), and NAA (0.01 mg/l). Higher numbers of buds were induced with the 2 weeks pulse treatment than were induced with the 1 week pulse treatment.

EXAMPLE 5

Excised cotyledons were pulse treated on a nutrient medium containing BAP (20 mg/l) and NAA (0.01 mg/l) for 1, 2, 3 and 4 weeks and then transferred to a bud growth medium (½ GD and charcoal 1%).

The following comparative examples were also run. (C1): Intact embryos cultured on standard bud induction medium (GD, BAP (10 mg/l), and ABA (0.03 mg/l)) for 8 weeks [Cello, L. and Smeltzer, R. H., 1977. CRC report]; and (C2): excised cotyledons cultured on standard bud induction medium (GD, BAP (1 mg/l) and NAA (0.01 mg/l) for 8 weeks [Mehra-Palta, A. Smeltzer, R. H. and Mott, R. L. 1978 Tappi 61, 37].

Buds appeared on the excised cotyledons 2 to 3 weeks after culture by pulse treatment, whereas in the comparative techniques, the buds appeared only after 4 to 6 weeks of culture. As summarized in Table 4 below, the results show that a greater number of buds were induced with the pulse treatment method than were induced with the comparative methods.

TABLE 4*

| Treatment | # embryos** planted | # embryos*** with buds | % embryos*** with buds | Av. # buds/ embryo |
|---|---|---|---|---|
| 1 week | 47 | 44 | 93 | 24 |
| 2 weeks | 200 | 194 | 97 | 49 |
| 3 weeks | 48 | 47 | 97 | 58 |
| 4 weeks | 45 | 43 | 95 | 55 |
| Comparative | | | | |
| (C1) 8 weeks | 48 | 26 | 54 | 6 |
| (C2) 8 weeks | 48 | 43 | 83 | 15 |

*Data for the 1, 2, 3 and 4 weeks pulse treatment were taken after 8 weeks culture on bud growth medium (½ GD + charcoal 1%).
**"embryos" actually represent a unit of 8 excised cotyledons from an embryo.
***"embryos" represent cotyledons making buds.

Figure 2:
FIG. 2 is a photograph of excised cotyledons after 7 days of culture, as reported in Example 4, on a bud induction medium comprising GD medium, 6-benzylaminopurine (BAP) 20 mg/l, and α-napthaleneacetic acid (NAA) 0.01 mg/l.
Figure 3:
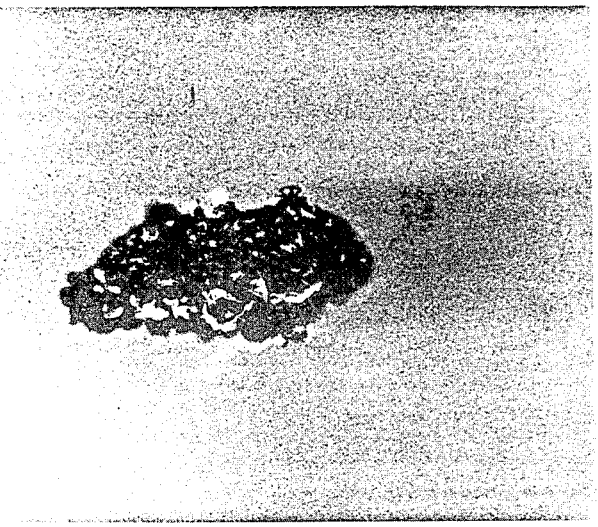
FIG. 3 is a photograph of a magnified view of one of the excised cotyledons of FIG. 2 four weeks after pulse treatment (three weeks on bud induction medium plus one week on bud growth medium) and placed on a nutrient medium free of exogenous growth factors and comprising ½ GD + charcoal 1%. Numerous bud primordia are visible.

Ten embryos were selected at random from those pulse treated for 2 weeks and the number of adventitious buds per embryo counted. The results are summarized in Table 5, below. A maximum of 295 buds/embryo was obtained with an average of 50 buds/embryo. Excised cotyledons from one embryo after 7 days of culture are shown in FIG. 2. Bud primordia appeared as small protuberances over the surface of the cotyledons. A magnified view of a single cotyledon with adventitious buds, 4 weeks after culture, is shown in FIG. 3.

TABLE 5

| Embryo # | Total # buds/embryo |
|---|---|
| 1 | 20 |
| 2 | 28 |
| 3 | 21 |
| 4 | 134 |
| 5 | 295 |
| 6 | 59 |
| 7 | 32 |
| 8 | 37 |
| 9 | 31 |
| 10 | 63 |

Adventitious buds were transferred to bud growth medium (½ GD and charcoal 1%). The bud growth results are summarized in Table 6, below.

TABLE 6*

| Treatment | # buds cultured | # buds >5 mm | % buds >5 mm |
|---|---|---|---|
| 1 week pulse | 727 | 597 | 82 |
| 2 week pulse | 2653 | 2216 | 85 |
| 3 week pulse | 995 | 684 | 68 |
| 4 week pulse | 1013 | 643 | 63 |
| Comparative Examples | | | |
| (C1) | 156 | 76 | 48 |
| (C2) | 645 | 91 | 14 |

*Data taken 12 weeks after the start of the initial induction treatment.

Although increased bud induction was obtained with the 3 and 4 week pulse treatments, the time period required for these buds to elongate into shoots also increased, by 4 to 10 weeks. The growth of the buds obtained by the 2 week pulse treatment was superior as compared to the bud growth obtained by the 3 and 4 week pulse treatments.

EXAMPLE 6

Figure 4:
FIG. 4 is a photograph of one of the excised cotyledons of FIG. 2 eight weeks after pulse treatment and shows the elongation of some adventitious buds into defined shoots.
Figure 5:
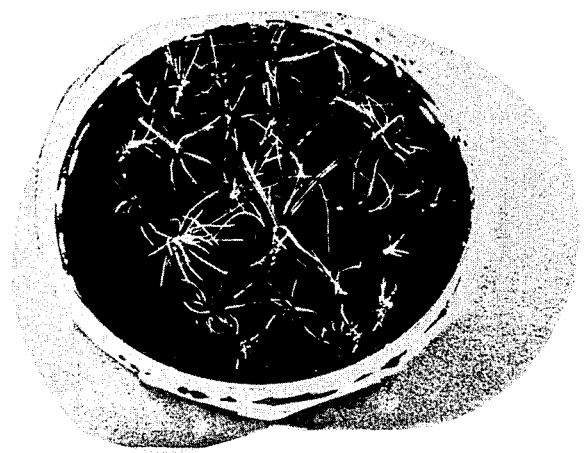
FIG. 5 is a photograph of adventitious shoots ready for planting on root induction medium.

To obtain rootable shoots, some of the adventitious buds from the two week pulse treatment in Example 5 were transferred to fresh bud growth medium (½ GD+charcoal 1%) after 4 weeks culture on the initial bud growth medium. FIG. 4 shows a cotyledon wherein some of the adventitious buds have elongated into defined shoots. At this stage, buds that had elongated were cultured separately, and those that had not were left intact on the cotyledons. After another 4 weeks, all of the elongated buds were isolated and subcultured onto fresh bud growth medium (½ GD+charcoal 1%) to allow the buds to form rootable shoots. The average bud growth frequency of adventitious buds after 2 weeks pulse treatment is reported in Table 7, below, wherein embryos were put into groups of tens at random. Up to 90% of the buds elongated to form rootable shoots. FIG. 5 shows elongated shoots ready for treatment on root induction medium.

TABLE 7

| Embryo #s | Total # buds cultured on bud growth medium | # buds >5 mm | % buds >5 mm |
|---|---|---|---|
| 1–10 | 2653 | 2216 | 86.5 |
| 11–20 | 2100 | 1762 | 83.9 |
| 21–30 | 994 | 855 | 86.0 |
| 31–40 | 763 | 591 | 77.0 |
| 41–50 | 484 | 481 | 91.1 |

EXAMPLE 7

Figure 6:
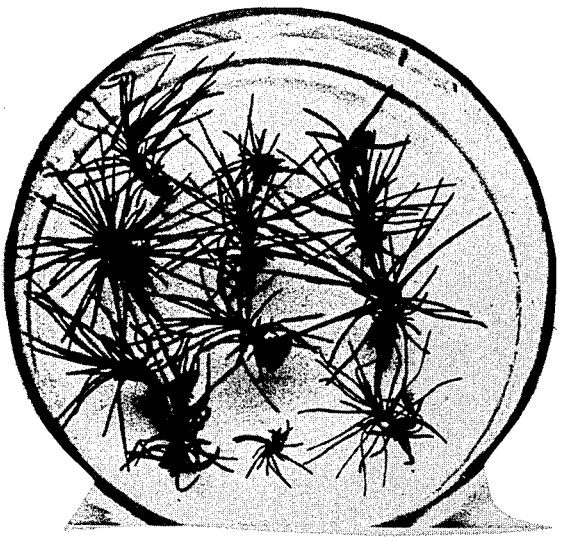
FIG. 6 is a photograph of rooted shoots or propagules 6 weeks after culture on rooting medium comprising ½ GD, Coumaric acid (CA) 10 mg/l, and indole-3-butyric acid (IBA) 10 mg/l.

Adventitious shoots from Example 6, 10 mm long or longer, were treated for from 4 to 6 weeks on different root induction media to determine their rooting potential. To avoid clonal effects on rooting, shoots were used from a minimum of 4 different genotypes for each treatment. Eight different phenolics, reported to be endogenously present in pines, were tested at a uniform concentration of 10 mg/l, with or without indole-3-butyric acid (IBA) at 10 mg/l. The pulse treated shoots were then transferred to root elongation media (½ GD and charcoal 1%) for 4 weeks and the number of shoots that rooted were counted. Controls were maintained on the standard root induction medium consisting of ½ GD, BAP (0.1 mg/l) and NAA (0.1 mg/l) for 8 weeks. The results are summarized in Table 8, below. FIG. 6 shows shoots rooted on the CA and IBA containing nutrient medium.

TABLE 8

| Medium | # shoots cultured | # shoots rooted | % shoots rooted |
|---|---|---|---|
| $BAP_{0.1}$* $NAA_{0.1}$ (Control) | 40 | 11 | 27.5 |
| $FA_{10}$ $IBA_{10}$ | 22 | 19 | 86.3 |

TABLE 8-continued

| Medium | # shoots cultured | # shoots rooted | % shoots rooted |
|---|---|---|---|
| CA$_{10}$IBA$_{10}$ | 24 | 22 | 91.6 |
| PBA$_{10}$IBA$_{10}$ | 24 | 13 | 54.1 |
| CTO$_{10}$IBA$_{10}$ | 24 | 15 | 62.5 |
| CLA$_{10}$IBA$_{10}$ | 24 | 15 | 62.5 |
| ICA$_{10}$IBA$_{10}$ | 20 | 7 | 35.0 |
| VA$_{10}$IBA$_{10}$ | 20 | 11 | 55.0 |
| CFA$_{10}$IBA$_{10}$ | 20 | 4 | 20.0 |
| IBA$_{10}$ | 40 | 26 | 65.0 |

*The subscript indicates the concentration of that growth regulator in mg/L.
FA = ferulic acid
CA = coumaric acid
PBA = p-hydroxybenzoic acid
CTO = catechol
CLA = chlorogenic acid
ICA = isochlorogenic acid
VA = vanillic acid
CFA = caffeic acid
IBA = indole-3-butyric acid

EXAMPLE 8

Figure 7:
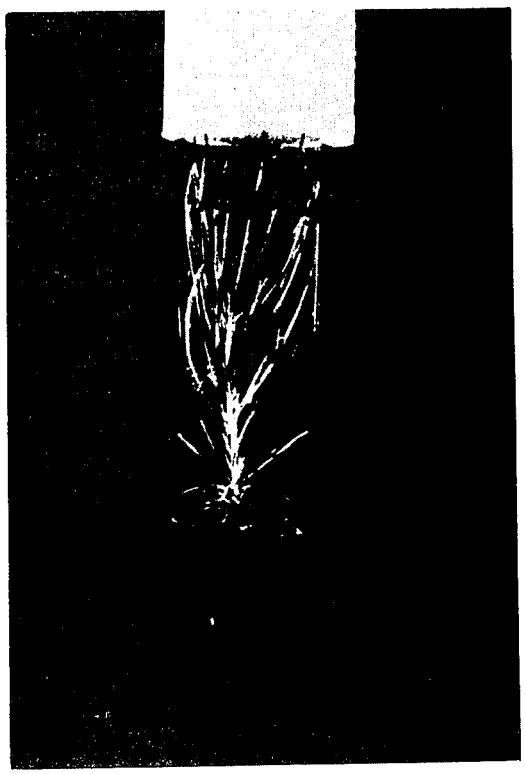
FIG. 7 is a photograph of a propagule cultured on a medium comprising ½ GD and charcoal 1% for root elongation.

Some shoots from Example 7 were transferred, after 4 weeks culture on the phenolic containing media, to root elongation medium comprising ½ GD and charcoal 1% for 4 weeks at which time roots had grown out to a length of from about 2 cm to about 5 cm (see FIG. 7), and were then transplanted into soil in a greenhouse and maintained under mist for about 1 month before transfer to standard greenhouse conditions.

Figure 8:
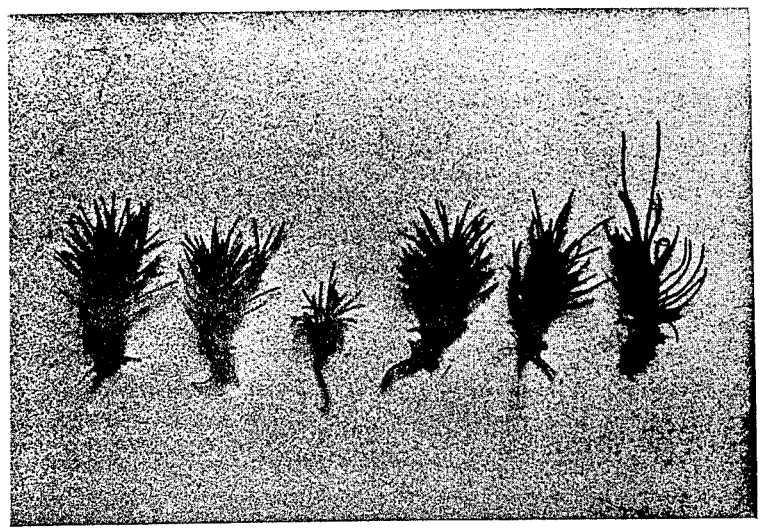
FIG. 8 is a photograph of 6-propagules obtained from one clone and ready for outplanting.
Figure 9:
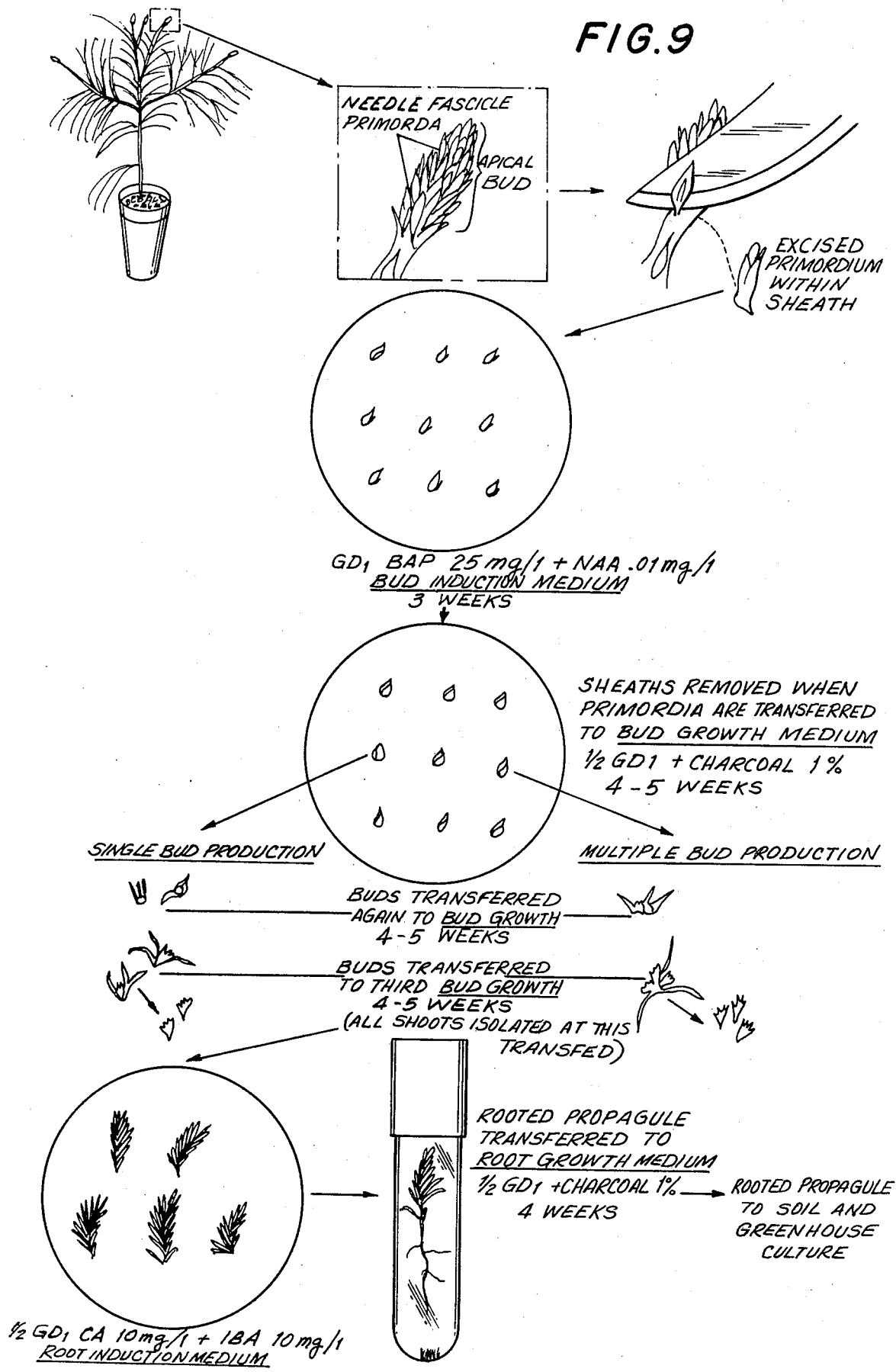
FIG. 9 is a schematic diagram of a process inclusive of another preferred embodiment of the present invention and showing use of neddle fascicles, another preferred excised gymnosperm tissue, and showing preferred concentrations, nutrient media and treatment times.
Figure 14:
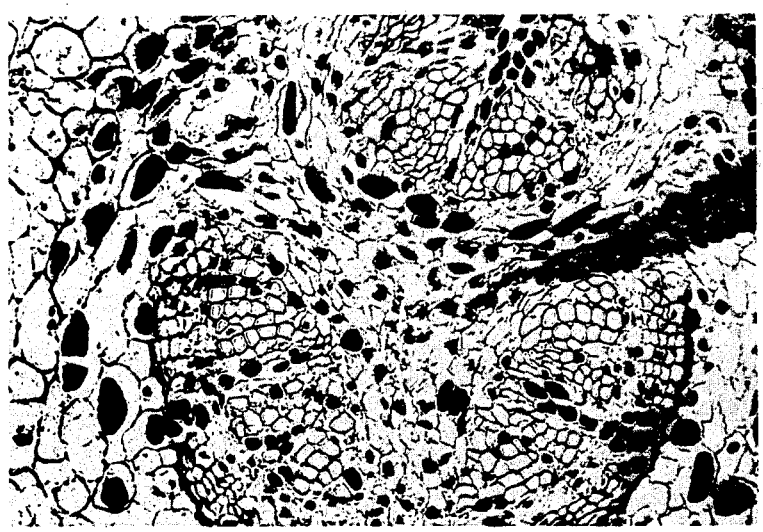
FIG. 14 is a photograph of a magnified view of a transverse section of a needle fascicle showing dormant shoot primordia activated to form adventitious bud primordia.
Figure 15:
FIG. 15 is a photograph of a magnified view of a transverse section of a needle fascicle showing multiple shoot primordia.

Propagules obtained by the treatments of Examples 5 through 8 were morphologically better developed as compared to those obtained by previous techniques such as the techniques employed in comparative examples C1 and C2. The propagules obtained were 2 cm to 5 cm long with a distinct stem, and well developed shoot and root systems; thus having a better chance of survival when transplanted into soil. FIG. 8 shows 6 such propagules, from one clone, just before outplanting into soil. Propagules developed by the previous techniques sometimes had no distinct stem and the needles arose in a bunch. They were much shorter, 5 mm to 10 mm, in length and the shoot and root systems were not very well developed. Thus, the pulse treatment method provides a method whereby the number of buds induced, the bud growth, and the rooting potential may be increased, thus allowing the production of larger clone size and in shorter times.

EXAMPLE 9

Needle fascicles at developmental stage 3 were pulse-treated for two weeks on a medium containing BAP and NAA (0.01 mg/L). The needle fascicles were divided into five groups and pulse-treated for two weeks on media containing the aforementioned concentration of NAA but a different concentration of BAP which was either 10, 20, 50, 100, or 200 mg/L. The pulse-treated fascicles were then transfered to a bud growth medium free of exogenous growth factors. As a control, needle fascicles were treated on a medium containing BAP (2.5 mg/L) and NAA (0.01 mg/L) for six to eight weeks. The results are summarized below in Table 9.

TABLE 9

Influence Of Different BAP Concentrations On Bud Induction Potential Of Needle Fascicles Pulse-Treated For Two Weeks

| Medium, mg/L | Needle Fascicles Swollen, (%) | Needle Fascicles With Buds, (%) |
|---|---|---|
| BAP 2.5 + NAA 0.01 | 55 | 17 |
| BAP 10 + NAA 0.01 | 79 | 60 |

TABLE 9-continued

Influence Of Different BAP Concentrations On Bud Induction Potential Of Needle Fascicles Pulse-Treated For Two Weeks

| Medium, mg/L | Needle Fascicles Swollen, (%) | Needle Fascicles With Buds, (%) |
|---|---|---|
| BAP 20 + NAA 0.01 | 87 | 52 |
| BAP 50 + NAA 0.01 | 85 | 57 |
| BAP 100 + NAA 0.01 | 87 | 63 |
| BAP 200 + NAA 0.01 | 15 | 0 |

EXAMPLE 10

Needle fascicles were pulse-treated for one hour, 24 hours, and 1, 2, 3, and 4 weeks on culture media containing BAP (50 mg/L) and NAA (0.01 mg/L), or BAP (100 mg/L) and NAA (0.01 mg/L), or BAP (25 mg/L) and NAA (0.01 mg/L). With the one hour and 24 hour treatments, no buds were obtained but the needle fascicles did elongate. Optimal bud induction occurred with the three weeks pulse-treatment. The highest bud induction frequency was obtained on the medium containing 25 mg/L of BAP.

As a control, needle fascicles were treated for the same time periods on a medium containing 2.5 mg/L of BAP and 0.01 mg/L of NAA. The results of the three week treatment are summarized in Table 10 below.

As shown in FIG. 11, the needle fascicles showed swelling at the basal region after two to three weeks of treatment on the medium containing 25 mg/L of BAP. When these treated fascicles were disected, as shown in FIG. 12, adventitious bud primordia could be seen.

TABLE 10

Influence Of BAP Concentrations On Needle Fascicle Bud Induction After Pulse Treatment For 3 Weeks

| Medium, mg/L | No. of Needle Fascicles | Needle Fascicles Swollen, (%) | Needle Fascicles With Buds, (%) |
|---|---|---|---|
| BAP 25 + NAA 0.01 | 100 | 70 | 67 |
| BAP 50 + NAA 0.01 | 100 | 55 | 45 |
| BAP 100 + NAA 0.01 | 100 | 80 | 58 |
| BAP 2.5 + NAA 0.01 (Control) | 50 | 68 | 19 |

EXAMPLE 11

In order to test for genetic differences in bud induction potential, needle fascicles from three half-sib seed families (7-105, 7-56, 7-88) were pulse-treated for three weeks on different media each of which contained 0.01 mg/L of NAA and which differed in the concentration of BAP which was either 25, 50, or 100 mg/L. As a control, needle fascicles from each seed family were treated on a medium containing 2.5 mg/L of BAP and 0.01 mg/L of NAA for six to eight weeks. The results are summarized below in Table 11.

TABLE 11

Bud Induction Potential Of Three Half-SIB Families After Pulse Treatment On Cytokinin Medium For 3 Weeks

| Seed Family | Medium, mg/L | No. of Needle Fascicles | No. of Needle Fascicles With Buds | Needle Fascicles With Buds, (%) |
|---|---|---|---|---|
| 7-56 | BAP 25 + NAA 0.01 | 100 | 59 | 66 |
| | BAP 50 + NAA 0.01 | 100 | 40 | 50 |
| | BAP 100 + NAA 0.01 | 100 | 37 | 39 |
| | BAP 2.5 + NAA 0.01 | 50 | 2 | 10 |
| 7-105 | BAP 25 + NAA 0.01 | 100 | 60 | 67 |
| | BAP 50 + NAA 0.01 | 100 | 40 | 42 |

TABLE 11-continued

Bud Induction Potential Of Three Half-SIB Families
After Pulse Treatment On Cytokinin Medium For 3 Weeks

| Seed Family | Medium, mg/L | No. of Needle Fascicles | No. of Needle Fascicles With Buds | Needle Fascicles With Buds, (%) |
|---|---|---|---|---|
| | BAP 100 + NAA 0.01 | 100 | 11 | 16 |
| | BAP 2.5 + NAA 0.01 | 50 | 4 | 13 |
| 7-88 | BAP 25 + NAA 0.01 | 100 | 29 | 42 |
| | BAP 50 + NAA 0.01 | 100 | 35 | 41 |
| | BAP 100 + NAA 0.01 | 100 | 17 | 21 |
| | BAP 2.5 + NAA 0.01 | 50 | 7 | 16 |

EXAMPLE 12

To evaluate the influence of the developmental stage of the needle fascicles on bud induction, needle fascicles at each of these five developmental stages were pulse-treated on a medium containing 25 mg/L of BAP and 0.01 mg/L of NAA for three weeks and then transferred to a bud growth medium free of exogenous growth factors. As a control, needle fascicles were also treated on a medium containing 2.5 mg/L of BAP and 9.01 mg/L of NAA for six weeks. The results are summarized in Table 12 below.

TABLE 12

Influence Of The Developmental Stage Of Needle Fascicles On Bud Induction

| Stage of Develop-ment | Needle Fascicles Swollen (%) | | Needle Fascicles With Buds, (%) | |
|---|---|---|---|---|
| | Medium I* | Medium II* | Medium I* | Medium II* |
| 1 | 61 | 72 | 2 | 8 |
| 2 | 52 | 71 | 0 | 29 |
| 3 | 66 | 91 | 14 | 63 |
| 4 | 22 | 75 | 4 | 18 |
| 5 | 24 | 31 | 7 | 3 |

*Medium I (Control) - BAP 2.5 mg/L + NAA 0.01 mg/L for six weeks.
Medium II - BAP 25 mg/L + NAA 0.01 mg/L for three weeks followed by transfer to bud growth medium.

EXAMPLE 13

Needle fascicles were treated on one of three bud induction media, each of which contained 0.01 mg/L of NAA and either 25, 50, or 100 mg/L of BAP, for three weeks and were then removed from the bud induction media, the needle fasicle sheaths removed and the needle fascicles transferred to bud growth medium free of exogenous growth factors and comprising ½ GD and charcoal (1%). The number of induced buds ranged from 1 to 8 with the average being 3. Needle fascicles at this stage and showing numerous adventitious buds are shown in FIG. 18.

EXAMPLE 14

Needle fascicles taken from two seed families (7-56 and 7-105) were pulse-treated for three weeks on three different bud induction media each of which contained 0.01 mg/L of NAA and either 25, 50, or 100 mg/L of BAP. As a control, needle fascicles from the same seed families were treated for six weeks on a medium containing 2.5 mg/L of BAP and 0.01 mg/L of NAA. The results are summarized in Table 13 below. In FIG. 19 are shown elongated shoots ten weeks after culture on bud growth medium free of exogenous growth factors.

TABLE 13

Bud Growth Frequency Of Adventitious Buds From Two Half-SIB Families

| Family | Medium, mg/L | No. of Buds Induced | No. of Buds E-longated | Bud Growth, Frequency, (%) |
|---|---|---|---|---|
| 7-56 | BAP 25 + NAA 0.01 | 169 | 164 | 97 |
| | BAP 50 + NAA 0.01 | 89 | 45 | 51 |
| | BAP 100 + NAA 0.01 | 75 | 41 | 55 |
| | BAP 2.5 + NAA 0.01 | 4 | 1 | 25 |
| 7-105 | BAP 25 + NAA 0.01 | 159 | 112 | 70 |
| | BAP 50 + NAA 0.01 | 40 | 19 | 47 |
| | BAP 100 + NAA 0.01 | 34 | 23 | 66 |
| | BAP 2.5 + NAA 0.01 | 5 | 1 | 20 |

EXAMPLE 15

Needle fascicle shoots which were initiated by pulse-treatment for three weeks on a nutrient medium containing BAP (50 mg/L) and NAA (0.01 mg/L) as well as shoots which had been initiated by pulse-treatment for three weeks on a medium containing 0.01 mg/L of NAA and 100 mg/L of BAP were pulse treated on two different media for about 4 to 6 weeks. One medium comprised ½ GD, 10 mg/L of CA, and 10 mg/L of IBA and the other medium comprised ½ GD, 5 mg/L of CA, and 5 mg/L of IBA. The results are summarized in Table 14 below. It was observed that some of the shoots callused profusely but that shoots that had a defined stem and were 0.5 cm or longer callused only at the cut end and formed roots. The formation of morphologically well defined shoots correlated well with high rooting frequencies.

TABLE 14

Rooting Frequency Of Adventitious Shoots Obtained From Different Bud Induction Media

| Bud Induction Medium, mg/L | Root Induction Medium, mg/L | Rooting Frequency, % |
|---|---|---|
| BAP 50 + NAA 0.01 | CA 10 + IBA 10 | 67 |
| BAP 100 + NAA 0.01 | CA 10 + IBA 10 | 53 |
| BAP 50 + NAA 0.01 | CA 5 + IBA 5 | 35 |
| BAP 100 + NAA 0.01 | CA 5 + IBA 5 | 60 |

EXAMPLE 16

Figure 20:
FIG. 20 is a photograph of shoots rooted on root induction medium comprising ½ GD, CA (10 mg/L), and IBA (10 mg/L).

Needle fascicles from two different seed families were pulse-treated on three different bud induction media for three weeks. Each of the media contained 0.01 mg/L of NAA and either 25, 50, or 100 mg/L of BAP. The resultant advantageous shoots were then pulse-treated on one of two root induction media one of which contained CA (10 mg/L) and IBA (10 mg/L) and the other of which contained CA (5 mg/L) and IBA (5 mg/L). No significant difference in root induction frequencies were observed on the two rooting media and therefore the results were grouped together and are summarized in Table 15 below. In FIG. 20 are shown rooted shoots six weeks after they were cultured on a medium comprising ½ GD, CA (10 mg/L), and IBA (10 mg/L).

Figure 21:
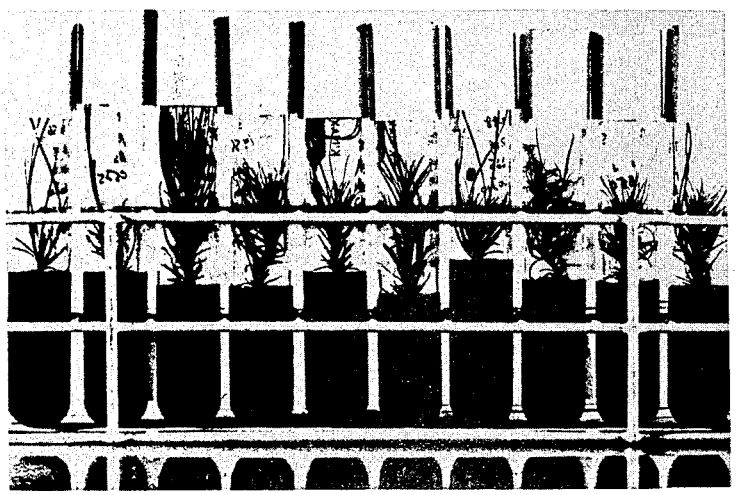
FIG. 21 is a photograph of a group of needle fascicle propagules produced according to the process of the present invention and ready for transplanting into soil.
Figure 22:
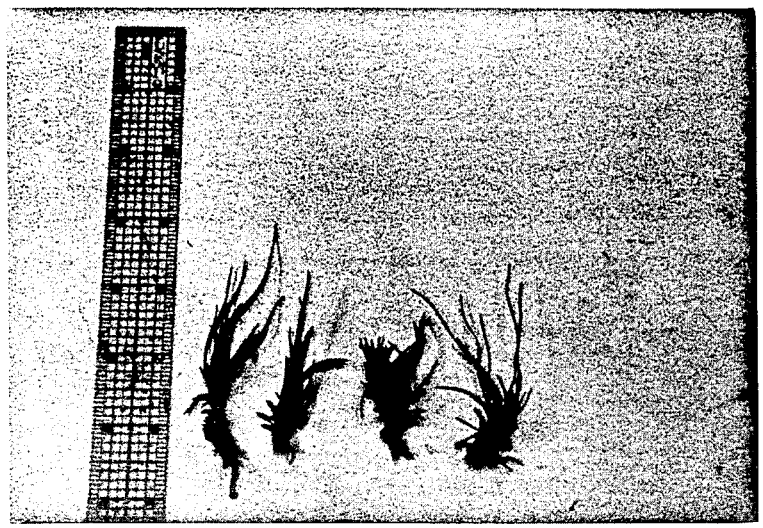
FIG. 22 is a photograph of a clone of four propagules produced according to the process of the present invention.
Figure 23:
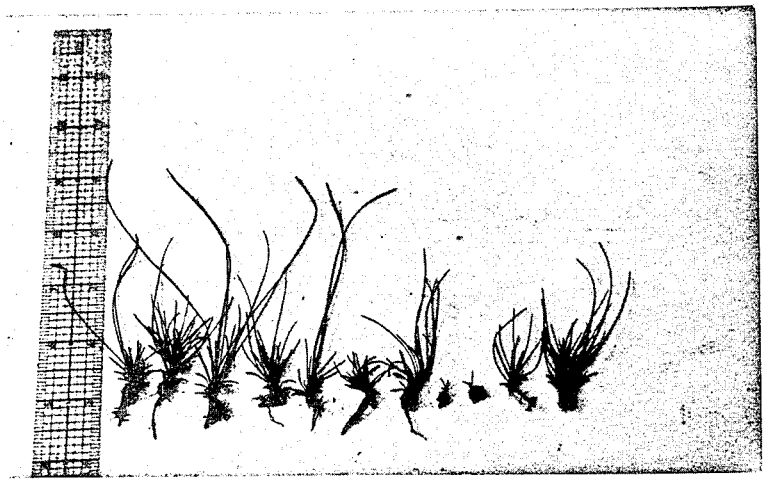
FIG. 23 is a photograph of a clone of 11 propagules also produced according to the process of the present invention.

After six weeks culture on the root induction medium, the rooted shoots were transferred to root elongation medium free of exogenous growth factors and comprising ½ GD, and charcoal (1%). After four to six weeks on the root elongation medium, the rooted plantlets (as shown in FIG. 21) were transferred into soil. In FIGS. 22 and 23 are shown, respectively, clones of 4 and 11 propagulas before transplanting into soil.

TABLE 15

Rooting Potential Of Adventitious Shoots From Two Seed Families

| Seed Family | Bud Induction Medium, mg/L | Root Induction Medium, mg/L | No. Shoots | No. Shoots Rooted | Rooting Frequency, % |
|---|---|---|---|---|---|
| 7-105 | BAP 25 + NAA 0.001 | CA 10 + IBA 10 | 112 | 47 | 44 |
|  | BAP 50 + NAA 0.001 | or | 19 | 11 | 58 |
|  | BAP 100 + NAA 0.01 | CA 5 + IBA 5 | 23 | 13 | 55 |
| 7-56 | BAP 25 + NAA 0.01 | CA 10 + IBA 10 | 164 | 51 | 28 |
|  | BAP 50 + BAA 0.01 | or | 55 | 6 | 15 |
|  | BAP 100 + NAA 0.01 | CA 5 + IBA 5 | 51 | 22 | 27 |

I claim:

1. A method of inducing formation of adventitious buds on excised gymnosperm tissue comprising pulse treating said tissue on a nutrient medium containing at least about 10 mg/L of a cytokinin for a time sufficient to induce formation of adventitious buds on said tissue, and then transferring the pulse treated tissue to a nutrient medium free of exogenous growth factors.

2. The method of claim 1 wherein the excised gymnosperm tissue is pulse treated for from about 1 week to about 4 weeks.

3. The method of claim 1 including maintaining the adventitious buds on the nutrient medium free of exogenous growth factors until the adventitious buds produce rootable shoots and then rooting the shoots.

4. The method of rooting shoots comprising pulse treating shoots on a nutrient medium containing at least about 5 mg/L of a phenolic compound and at least about 5 mg/L of an auxin for a time sufficient to induce formation of adventitious roots and then transferring the pulse treated shoots to a nutrient medium free of exogenous growth factors until the roots grow out.

5. The method of claim 4 wherein the shoots are pulse treated for from about 2 weeks to about 6 weeks.

6. A method of in vitro clonal propagation of plantlets from excised gymnosperm tissue comprising:
   (a) pulse treating excised gymnosperm tissue on a nutrient medium containing at least about 20 mg/L of a cytokinin for a time sufficient to induce formation of adventitious buds on said tissue; then
   (b) transferring the pulse treated tissue to a nutrient medium free of exogenous growth factors until the induced adventitious buds produce rootable shoots; then
   (c) pulse treating said rootable shoots on a nutrient medium containing at least about 5 mg/L of a phenolic compound and at least about 5 mg/L of an auxin for a time sufficient to induce formation of adventitious roots; and then
   (d) transferring the treated shoots to a nutrient medium free of exogenous growth factors until the roots elongate.

7. The method of claim 6 wherein the excised gymnosperm tissue is pulse treated on the cytokinin-containing medium for from about 1 week to about 4 weeks.

8. The method of claim 7 wherein the cytokinin concentration is from about 20 mg/L to about 200 mg/L.

9. The method of claim 6 wherein the rootable shoots are treated on the medium containing the phenolic compound and the auxin for from about 2 weeks to about 6 weeks.

10. The method of claim 6 wherein said excised gymnosperm tissue is selected from the group consisting of cotyledons, needle fascicles, intact seed embryos, needles, shoot tips, apical buds, and hypocotyls.

11. The method of claim 10 wherein the excised gymnosperm tissue is from a conifer.

12. The method of claim 11 wherein the conifer is lobolly pine (Pinus taeda).

13. A method of in vitro clonal propagation of plantlets from excised conifer tissue comprising:
   (a) pulse treating excised conifer tissue on a nutrient medium containing from about 0.01 mg/L to about 0.1 mg/L of an auxin and from about 10 mg/L to about 200 mg/L of a cytokinin for from about 1 week to about 4 weeks to induce formation of adventitious buds on said tissue; then
   (b) transferring the pulse treated tissue to a nutrient medium free of exogenous growth factors until the induced adventitious buds produce rootable shoots; then
   (c) pulse treating said rootable shoots on a nutrient medium containing from about 5 mg/L to about 50 mg/L of a phenolic compound and from about 5 mg/L to about 50 mg/L of an auxin for from about 2 weeks to about 6 weeks to induce formation of adventitious roots; and then
   (d) transferring the treated shoots to a nutrient medium free of exogenous growth factors until the roots elongate.

14. The method of claim 13 wherein the excised conifer tissue is selected from the group consisting of cotyledons, needle fascicles, intact seed embryos, needles, shoot tips, apical buds, and hypocotyls.

15. The method of claim 14 wherein the excised conifer tissue is from lobolly pine (Pinus taeda).

16. The method of claim 13 or 15 wherein the cytokinin is selected from the group consisting of 6-benzylaminopurine, zeatin, kinetin and 2iP and mixtures thereof.

17. The method of claim 16 wherein the cytokinin is 6-benzylaminopurine.

18. The method of claim 17 wherein the cytokinin is present at a concentration of from about 20 mg/L to about 100 mg/L and the auxin, in step (a), is present at a concentration of from about 0.01 mg/L to about 0.05 mg/L.

19. The method of claim 16 wherein the phenolic compound is selected from the group consisting of coumaric acid, ferulic acid, p-hydroxybenzoic acid, catechol, vanillic acid, and caffeic acid, and mixtures thereof, and the auxins are selected from the group consisting of indole-3-butyric acid, indole-3-acetic acid, 2,4-dichlorophenoxyacetic acid, and α-napthaleneacetic acid, other auxins and mixtures thereof.

20. The method of claim 19 wherein in step (c) the phenolic compound is coumaric acid and the auxin is incole-3-butyric acid.

21. The method of claim 20 wherein the phenolic compound is present in an amount of about 10 mg/L and the auxin is present in an amount of about 10 mg/L.

22. The method of claim 19 wherein the auxin in step (a) is α-napthaleneacetic acid.

* * * * *